(12) United States Patent
Lill (10) Patent No.: US 11,191,534 B2
(45) Date of Patent: Dec. 7, 2021

(54) DEVICE FOR REDUCING THE RETRACTION OF A FASCIA OR A SOFT-TISSUE MANTLE IN AN OPEN SOFT-TISSUE DEFECT

(71) Applicant: Fasciotens GmbH, Essen (DE)

(72) Inventor: Gereon Lill, Cologne (DE)

(73) Assignee: Fasciotens GmbH, Essen (DE)

( * ) Notice: Subject to any disclaimer, the term of this patent is extended or adjusted under 35 U.S.C. 154(b) by 22 days.

(21) Appl. No.: 16/307,552

(22) PCT Filed: Jun. 14, 2017

(86) PCT No.: PCT/EP2017/064546
§ 371 (c)(1),
(2) Date: Dec. 6, 2018

(87) PCT Pub. No.: WO2017/216224
PCT Pub. Date: Dec. 21, 2017

(65) Prior Publication Data
US 2019/0150907 A1 May 23, 2019

(30) Foreign Application Priority Data
Jun. 14, 2016 (DE) .................. 10 2016 210 574.4

(51) Int. Cl.
*A61B 17/20* (2006.01)
*A61B 17/08* (2006.01)
(Continued)

(52) U.S. Cl.
CPC .......... *A61B 17/0293* (2013.01); *A61B 17/08* (2013.01); *A61B 2017/00561* (2013.01);
(Continued)

(58) Field of Classification Search
CPC ........ A61B 17/0293; A61B 2017/0287; A61B 17/02; A61B 17/0218; A61B 17/0206
See application file for complete search history.

(56) References Cited

U.S. PATENT DOCUMENTS 4,136,560 A * 1/1979 Gellos ................. B60C 23/0496
73/146.8
4,926,849 A 5/1990 Downey
(Continued)

FOREIGN PATENT DOCUMENTS

CN 103402441 A 11/2013
CN 203802512 U 9/2014
(Continued)

OTHER PUBLICATIONS

International Search Report for International Application No. PCT/EP2017/064546; dated Aug. 29, 2017.
(Continued)

*Primary Examiner* — Kevin T Truong
*Assistant Examiner* — Lisa Nguyen
(74) *Attorney, Agent, or Firm* — The Dobrusin Law Firm, P.C.

(57) ABSTRACT

A device for reducing retraction of edges of an opened fascia of a patient having an open soft-tissue defect. The device includes a holding element and an attachment element. The holding element is configured to be fixed with respect to the patient at a first distance from the patient. The attachment element has a plurality of attachment points configured for attaching tensioning means, which is configured to be connected to an edge of the fascia. The attachment element being connected to the holding element so as to be arranged at a second distance from the patient, which is less than the
(Continued)

first distance. The attachment element is connected to the holding element via exactly one tensile force transmission element.

27 Claims, 7 Drawing Sheets

(51) Int. Cl.
*A61B 17/00* (2006.01)
*A61B 90/00* (2016.01)
*A61B 17/02* (2006.01)

(52) U.S. Cl.
CPC .............. *A61B 2017/00659* (2013.01); *A61B 2017/0287* (2013.01); *A61B 2017/081* (2013.01); *A61B 2090/064* (2016.02)

(56) References Cited

U.S. PATENT DOCUMENTS

| | | | |
|---|---|---|---|
| 5,603,689 A | | 2/1997 | Lucini |
| 6,354,994 B1 | | 3/2002 | Rullo et al. |
| 10,123,790 B2 * | | 11/2018 | Lill .................. A61B 17/08 |
| 2008/0319487 A1 | | 12/2008 | Fielding et al. |
| 2013/0123828 A1 | | 5/2013 | Culmer et al. |
| 2013/0190572 A1 | | 7/2013 | Lee |
| 2014/0221736 A1 * | | 8/2014 | Cohen ................ A61B 17/0057 600/37 |
| 2017/0035405 A1 | | 2/2017 | Lill |

FOREIGN PATENT DOCUMENTS

| | | | | |
|---|---|---|---|---|
| DE | 29507627 U1 | | 7/1995 | |
| DE | 102014209995 A1 | * | 10/2015 | ............. A61B 17/02 |
| EP | 3123947 A1 | * | 2/2017 | ............. A61B 90/02 |
| JP | S58159736 A | | 9/1983 | |
| JP | H0454954 A | | 2/1992 | |
| JP | 2003/532480 A | | 11/2003 | |
| JP | 2010/530780 A | | 9/2010 | |
| WO | 2015/155176 A1 | | 10/2015 | |

OTHER PUBLICATIONS

Shinohara, Successful Sequential Sac Ligation for an Unruptured Giant Omphalocele, Report of a Case in Surgery Today, vol. 36 (2006) Issue 8, pp. 707-709.

Baird, Management of a Giant Omphalocele with an External Skin Closure System in Journal of Pediatric Surgery, vol. 45 (2010), Issue 7, pp. E17-E20.

Search Report for Application No. 10 2016 210 574.4, created on Jun. 13, 2017.

Written Opinion of the International Search Authroty for Application PCT/EP2017/064546 dated Aug. 22, 2017.

Japanese Office Action for Japanese Application 2018-565796, dated May 15, 2020.

Chinese First Search for Chinese Application 2017800315836, dated Sep. 7, 2020.

Japanese Notice of Reasons for Refusal for Japanese Application 2018-565796, dated Sep. 7, 2020.

* cited by examiner

DEVICE FOR REDUCING THE RETRACTION OF A FASCIA OR A SOFT-TISSUE MANTLE IN AN OPEN SOFT-TISSUE DEFECT

FIELD OF THE INVENTION

The invention relates to a device for reducing the retraction of the edges of an opened fascia of a patient having an open soft-tissue defect, the device having a holding element, which can be fixed with respect to the patient at a first distance from the patient, and an attachment element which has a plurality of attachment points configured for attaching tensioning means, which can be connected to an edge of the fascia, the attachment element being connected to the holding element so as to be arranged at a second distance from the patient which is less than the first distance.

The invention further relates to a kit for treating an open soft-tissue defect comprising at least one sponge for filling out the soft-tissue defect.

The invention may be applied in the case of open soft-tissue defects and/or open wounds. Soft-tissue defects or wounds may for example take the form of a stomach wall defect, back wall defect, soft-tissue defect in the region of the hips or soft-tissue defect on the limbs.

BACKGROUND

A device for reducing the retraction of the edges of an opened fascia of a patient having an open soft-tissue defect is known from WO 2015/155176 A1. By means of this device, a tensile force can be applied to the edges of the opened fascia. The edges of the opened fascia are held at a distance, in such a way that access to the internal body space positioned below the soft-tissue defect, for example the abdomen, is possible, for example so as to carry out a negative pressure wound treatment. As a result of the tensile force, the tension in the fascia is maintained and the retraction of the edges of the fascia is thus reduced. After the treatment is concluded, the edges of the fascia can be laid against one another and sealed directly.

To carry out a negative pressure wound treatment, it is necessary to seal off the open soft-tissue defect or the open walls in such a way that a negative pressure can be generated. For sealing, for example gas-tight films may be used, which define a negative pressure region sealed off from the environment. The known device has a holding element which can be fixed with respect to the patient at a first distance from the patient. The holding element is connected via a plurality of cords to an attachment element, which has a plurality of attachment points which are set up for attaching tension means. The tension means are connected to an edge of the fascia, in such a way that a tensile force acts on the fascia. The attachment element is arranged at a second distance from the patient, which is less than the first distance. When a vacuum wound treatment is carried out, the device is typically arranged within the negative pressure region. To make it possible to retension the tension means or the cables even when a negative pressure is being applied, an actuation element, arranged outside the sealed-off region, is provided on the holding element. To make the negative pressure wound treatment possible, the holding element is formed with a sealed-off housing and sealed off with respect to the gas-tight film at a plurality of points. For sealing off the negative pressure region, a considerable number of hand movements are therefore required.

SUMMARY

Against this background, the object of the invention is to make it possible to seal off the negative pressure region using as few hand movements as possible.

The object is achieved by a device for reducing the retraction of the edges of an opened fascia of a patient having an open soft-tissue defect, the device comprising a holding element which can be fixed with respect to the patient at a first distance from the patient, and an attachment element, which has a plurality of attachment points which are set up for attaching tension means, which can be connected to an edge of the fascia, the attachment element being connected to the holding element in such a way that it is arranged at a second distance from the patient, which is less than the first distance, the attachment element being connected to the holding element via exactly one tensile force transmission element.

According to the invention, the attachment element is connected to the holding element via exactly one tensile force transmission element, which transmits the entire tensile force from the attachment element to the holding element. When a negative pressure wound treatment is being carried out, the holding element can be arranged outside the negative pressure region and hold the attachment element, which is arranged within the negative pressure region.

Since there is merely one connection between the holding element and the attachment element, sealing off the negative pressure region is facilitated. A film which delimits the negative pressure region only has to be sealed off with respect to the tensile force transmission element at one point. It is thus made possible to seal off the negative pressure region using few hand movements.

The holding element can be fixed to the body of the patient, in such a way that the holding element can move with the patient when he changes position. A preferred embodiment provides that the holding element is formed as a rod. The holding element can preferably be arranged parallel to a body surface of the patient. The attachment may take place via a fastening means, in particular a belt fastening and/or a prop, which can be fixed to the body of the patient. A plurality of fastening means may be provided. A configuration comprising two fastening means, which can be arranged in the upper (cranial) and lower (caudal) region of the abdomen or back, is preferred. Preferably, the fastening means is formed in such a way that it can be positioned on the skin of the patient or can be fixed a bone of the patient. The fastening may for example take place at the sternum and/or at the front pelvic ring. Preferably, the fastening means is provided in such a way that it can be positioned on the skin in a region in the vicinity of the soft-tissue defect, in which the device does not apply any tensile forces to the fascia positioned under the skin. A further preferred embodiment provides that the fastening means has a pressure distribution means, which can be positioned on the skin of the patient. The pressure distribution means may have a cushion, in particular a foamed material cushion. The pressure distribution means can preferably be filled with a medium. A gas, in particular air, a liquid, in particular water, or a gel, may be used as the medium for filling the pressure distribution means. The pressure distribution means may have a chamber into which the medium can be introduced. Via the pressure distribution means, compressive forces acting on the skin of the patient can be distributed uniformly, in such a way that the risk of pressure points forming on the skin is reduced. Particularly preferably, the fastening means has a pressure distribution means comprising a plurality of chambers, in particular two. It is advantageous if the chambers are formed in such a way that they can be filled with a medium in turn, in such a way that the compressive forces can be introduced into different regions of the skin in turn. The chambers are preferably formed in the manner of concentric circles, the first chamber being formed as a circular ring which encloses a second chamber.

A preferred embodiment of the invention provides that the device has a plurality of props which each connect the holding element to a pressure distribution means which can be positioned on the skin of the patient. As a result, the holding element can be arranged at the first distance and in front of the open soft-tissue defect.

In a preferred embodiment, the fastening means has an implant, which can be fixed to a bone of the patient. The implant may be formed internally or externally as a fixator. The implant is particularly preferably an implant which is already present in the body of the patient, such as a spinal column implant. Alternatively, it is possible to introduce the implant together with the device for reducing the retraction of the fasciae. The implant may have one or more longitudinal supports. The longitudinal supports of the implant can be fastened to bones of the patient, for example to vertebral bodies of the spinal column. For fastening the implant, in particular the longitudinal supports, to the bones, the implant preferably comprises one or more connection means, in particular one or more screws.

It is preferred for the device to have a plurality of props which connect the holding element to an implant or a plurality of implants which can be fixed to a bone of the patient.

Preferably, the tensile force transmission element is guided in a recess in the holding element, in such a way that the tensile force transmission element can be moved to set the distance between the holding element and the attachment element. The tensile force transmission element can thus be moved in a direction orientated transverse, in particular perpendicular, to the body surface.

In a preferred embodiment, a sealing element is arranged on the tensile force transmission element. A film for sealing off the negative pressure region may be attached to the sealing element. The sealing element may be formed as a sealing ring. Preferably, the sealing element is arranged displaceable along the tensile force transmission element, in such a way that the tensile force transmission element can be moved, in particular rotated, without detracting from sealing applied to the sealing element. The sealing element may have an internal thread which is engaged with an external thread arranged on the tensile force transmission element.

In a preferred embodiment, the tensile force transmission element has an air duct. If the holding element is arranged outside the negative pressure region and the attachment element is arranged inside the negative pressure region, via the air duct of the tensile force transmission element a negative pressure can be generated in the negative pressure region. To form the air duct, the tensile force transmission element may be formed hollow, for example as a pipe or hose.

Preferably, the air duct connects a first opening for attaching a vacuum pump to a second opening arranged in the region of the attachment element. An attachment connector for attaching the vacuum pump may be provided at the first opening. The first opening and the second opening may for example be arranged at two opposite end faces of the tensile force transmission element. Preferably, the device has a closure by means of which the air duct can be selectively sealed.

An advantageous embodiment provides that the device has a tensile force gauge for measuring the tensile force transmitted via the tensile force transmission element. The tensile force gauge is preferably formed as a spring balance. By means of the spring balance, the tensile force can be determined by way of the extension of a compression spring or a tension spring, in particular a compression coil spring or tension coil spring. Alternatively, the tensile force gauge may be configured as an inductive force gauge, capacitive force gauge, optical force gauge, strain gauge, magnetic force gauge, electromagnetic force gauge or piezoelectric force gauge. The tensile force gauge, in particular a display of the tensile force gauge, is preferably arranged between the holding element and the tensile force transmission element, in such a way that the display of the tensile force gauge can still be read off when the attachment element is arranged in the sealed-off negative pressure region.

Preferably, the tensile force gauge has a compression spring, which comprises a first spring end, which is mounted stationary with respect to the holding element, and a second spring end, which is mounted stationary with respect to a catch of the tensile force transmission element or with respect to a fastening element, in particular a nut, positioned on an external thread of the tensile force transmission element. The compression spring can bring about a tensile force on the edge of the fascia, which is transmitted via the tensile force transmission element, the attachment element and the tension means. Simultaneously, by way of the length of the compressed compression spring, the tensile force transmitted via the tensile force transmission element can be determined. For example, the first spring end can be positioned on the holding element and/or be connected to the holding element. The second spring end can be positioned on the catch of the tensile force transmission element or on the fastening element positioned on the external thread of the tensile force transmission element or be connected to the catch or the fastening element. It has been found to be advantageous for the compression spring of the tensile force gauge to be arranged concentric with the tensile force transmission element. The tensile force transmission element can thus move within the compression spring with respect to the first spring end, which is mounted stationary with respect to the holding element.

In an advantageous embodiment, the tensile force gauge has a scale sleeve and an indicator sleeve, which are arranged movable with respect to one another concentric with the tensile force transmission element. The scale sleeve may have a plurality of regions, in particular three, which are provided with different colours and/or hatchings and/or symbols.

Alternatively or in addition, the scale sleeve may have a scale display. Preferably, the indicator sleeve is of a greater diameter than the scale sleeve, in such a way that the indicator sleeve can enclose the scale sleeve from the outside. Preferably, the scale sleeve is fixed to the holding element and the indicator sleeve is fixed to the tensile force transmission element, in particular to a catch or to a fastening element positioned on an external thread of the tensile force transmission element. Alternatively, the indicator sleeve may be fixed to the holding element and the scale sleeve may be fixed to the tensile force transmission element, in particular to a catch or to a fastening element positioned on an external thread of the force transmission element.

It is particularly preferred for the tensile force gauge to have three or more sleeves, which are arranged movable with respect to one another concentric with the tensile force transmission element.

An embodiment is advantageous in which the tensile force transmission element is formed rigid. A rigid tensile force transmission element is understood to be in particular a tensile force transmission element via which a compressive force counter to the tensile force can be transmitted. The rigid tensile force transmission element may for example be formed as a rod, screw or pipe. Alternatively, the tensile force transmission element may be formed resilient, for example as a hose.

An embodiment has been found to be advantageous in which the attachment element is detachably connected to the holding element, in such a way that the holding element can be removed from the patient without it being necessary to detach the tension means from the edge of the fascia. Detachment of this type may be required in particular if the region around the soft-tissue defect has to be exposed, for example so as to be able to perform resuscitation measures on the patient.

Preferably, the device has a disconnection means, by means of which the connection between the holding element and the attachment element and/or the connection between the tensile force transmission element and the holding element and/or the connection between the attachment element and the tensile force transmission element can be detached. The disconnection means is preferably formed as a quick disconnect means, which can be disconnected using a hand movement. For example, the tensile force transmission element may be connected to the attachment element in such a way that it can be detached from the holding element together with the attachment element.

It is particularly preferred for the tensile force transmission element to have a first part and a second part which can be selectively connected to or separated from one another. An embodiment of this type has the advantage that the first part can be arranged in a sterile region and the second part can be arranged in a non-sterile region, or vice versa.

Preferably, a detachable coupling is arranged between the first part and the second part and connects the first part to the second part. The coupling is particularly preferably detachable manually, in other words without a tool, in such a way that the region of the soft-tissue defect can be exposed rapidly, for example if resuscitation measures are to be performed on the patient. For example, the coupling may be a plug-in coupling or a rotary coupling.

Preferably, the tensile force transmission element is connected to the holding element and/or to the attachment element via a joint. By way of the joint, it is possible to adjust the position of the attachment element with respect to the holding element. The hinge may be formed as a ball joint. Alternatively, the joint may be configured as a hinge joint. In an embodiment in which the tensile force transmission element has a first part and a second part, between which a coupling is arranged, the joint, in particular the ball joint, may be provided in the region of the coupling. The joint may be arranged either on the first part or on the second part of the tensile force transmission element.

An advantageous embodiment provides that the attachment element has two attachment regions, the attachment regions each having a plurality of attachment points and a distance of the first attachment region from the second attachment region being adjustable. Preferably, the two attachment regions are detachable from one another. Particularly preferably, the two attachment regions are detachable from one another and from the tensile force transmission element.

An advantageous embodiment provides that the attachment element has two attachment regions, the attachment regions each having a plurality of attachment points and the attachment regions being movable with respect to one another. Preferably, the distance of the first attachment region from the second attachment region is adjustable. The attachment regions may be connected via one or more telescopic connection elements, in particular telescopic bars. Preferably, the positioning of the attachment regions with respect to one another can be locked. The tensile force transmission element can be connected to one of the attachment regions. Preferably, a first attachment region is connected to the tensile force transmission element in such a way that a second attachment region is movable with respect to the first attachment region and the tensile force transmission element. The attachment regions may be formed as bars or pipes. The attachment regions may be formed straight or have a curvature. For example, it is possible for two attachment regions to be provided which are formed straight and which are arranged extending mutually parallel. Alternatively, it is possible for two curved attachment regions to be provided.

In this connection, it is advantageous if the attachment element has a base part and the attachment regions are movable with respect to the base part. Preferably, the base part is connected to the tensile force transmission element. Preferably, the base part is connected to the tensile force transmission element via a joint, in particular a ball joint or a hinge joint. Preferably, the positioning of the attachment regions with respect to the base part is lockable. The attachment regions may be connected to the base part via telescopic connection elements, in particular telescopic bars.

A preferred embodiment provides that the attachment regions are detachable from the base part. In an embodiment of this type, the attachment regions are separated from the base part so as to gain improved access to the open soft-tissue defect. It is therefore possible to work on the soft-tissue defect without having to detach the tension means from the attachment regions.

An embodiment is preferred in which the attachment element has a base part, the attachment regions being detachable from the base part and a plurality of connection points, to which the attachment regions can selectively be connected, being provided on the base part, in such a way that different distances between the attachment regions can be adjusted.

Particularly preferably, at the connection points, the base part has through-holes in each of which a securing element, in particular a securing bolt or a securing screw, is arranged. The securing bolt may be movable between a disconnection position, in which the attachment region is removable from the base part, and a connection position, in which the attachment region is fixed to the base part via the securing bolt. The securing bolt may be biased by way of a spring element, in particular towards the connection position. Particularly preferably, the securing bolt is formed as a latch bolt which is biased by way of a spring element and which can be selectively latched in the disconnection position.

It is advantageous if the device has at least one tension means which can be connected to the fascia. By way of the tension means, the tensile force can be introduced into the fascia. Preferably, a plurality of tension means are provided, by way of which tensile forces can be applied to the edges of the opened fascia at a plurality of different points. The different tension means may each introduce tensile forces of different strengths and different orientations into the fascia. Alternatively, the tension means may be connected to the surface of the body, in particular to the abdominal wall or the back wall, including the fascia, in such a way that not only the fascia, but also the skin positioned over the fascia is held tensioned.

Preferably, the tension means is formed as a thread and/or wire and/or net. Conventional threads, wires or nets used in surgery may be applied. Preferably, the tension means is formed as a combination of a thread and/or a wire and/or a net. It is further preferred if the tension means can be connected to the fascia via a connection means which is formed planar. By way of the planar connection means, improved attachment of the tension means to the fascia can be achieved. The risk of tearing out the fascia can be reduced, and the fascia can be treated gently if the tension means are repeatedly changed. An embodiment is particularly preferred in which the planar connection means can be sutured to the fascia.

Alternatively, the connection means may for example have hooks, in particular barbs, which can be introduced into the fascia. The connection means may for example be formed as a net or plate. The tension means may be connectable to the fascia and additionally to other components of the soft-tissue mantle, preferably to the entire soft-tissue mantle, via the connection means which is formed planar. For example, as well as the fascia, the skin may also be connected to the planar connection means. It is advantageous if the connection means which is formed planar is reversibly connected to the tension means, in such a way that the tension means and/or the suspension can be removed and attached again without difficulty, so as to treat the open soft-tissue defect, in particular the open abdomen or the open back.

An advantageous embodiment provides that the attachment element has a through-hole and an insertion groove opening into the through-hole, via which a tension means can be inserted into the through-hole, in the region of each of the attachment points. This has the advantage that a securing element which may be arranged in the through-hole, in particular a bolt or a screw, does not have to be fully removed from the through-hole so as to introduce the tension means into the through-hole. The attachment points are preferably arranged in the attachment regions of the attachment element.

An alternative embodiment of the attachment points provides that they have a conical through-opening in which a ball is arranged, by way of which a tension means passed through the through-opening can be gripped in the through-opening. The ball can be secured against undesired falling out of the conical through-hole by way of a securing element. Optionally, an insertion groove may be provided which opens into the conical through-opening.

A kit for treating an open soft-tissue defect comprising at least one sponge for filling out the soft-tissue defect, the kit having an above-described device, further contributes to achieving the object stated at the outset.

As a result, the same advantages can be achieved which were described previously in connection with the device according to the invention for reducing the retraction of the edges of an opened fascia of a patient.

An advantageous embodiment of the kit provides that the kit additionally has a sealing means for sealing off the open soft-tissue defect, in particular the abdomen or the open back. The sealing means may be formed as a film, which can be applied, in particular glued, to the side remote from the body of the sponge on the open soft-tissue defect, in particular the opened abdominal wall. As a result of the sealing means, the internal body space, in particular the abdomen or the space within the back wall, can be sealed in a liquid-tight and gas-tight manner. The sealing means can be arranged in such a way that the device for reducing the retraction of the edges of an opened fascia is positioned in whole or in part within the region sealed off by the sealing means. Preferably, the sealing means is formed as a non-adhesive, air-impermeable film. The non-adhesive, air-impermeable film can be positioned directly on the device for reducing the retraction of the fascia edges. The non-adhesive, air-impermeable film can be fixed on the body of the patient via adhesive means, for example an adhesive film.

The sealing means advantageously has an opening for passing the tensile force transmission element through. In the region of the opening of the sealing means, the sealing means may be connectable to the sealing element of the tensile force transmission element. The sealing element may be formed as an in particular resilient sealing ring. Preferably, the sealing means, in particular the film, may have in the region of the opening an adhesive means via which the sealing means can be connected in a sealing manner to the sealing element of the tensile force transmission element. The adhesive means may for example be formed as a self-adhesive region of the sealing means or as an adhesive element arranged on the sealing means.

Preferably, the kit has a vacuum pump for generating a negative pressure in the body interior, in particular in the abdomen or in the space positioned within the back wall, of the patient. By way of the vacuum pump, excess liquids and/or gases can be sucked out of the body interior, in particular the abdomen or the space positioned within the back wall.

BRIEF DESCRIPTION OF THE DRAWINGS

Further advantages and details of the invention are to be described hereinafter with reference to the embodiments shown in the drawings, in which.

DETAILED DESCRIPTION

Figure 1:
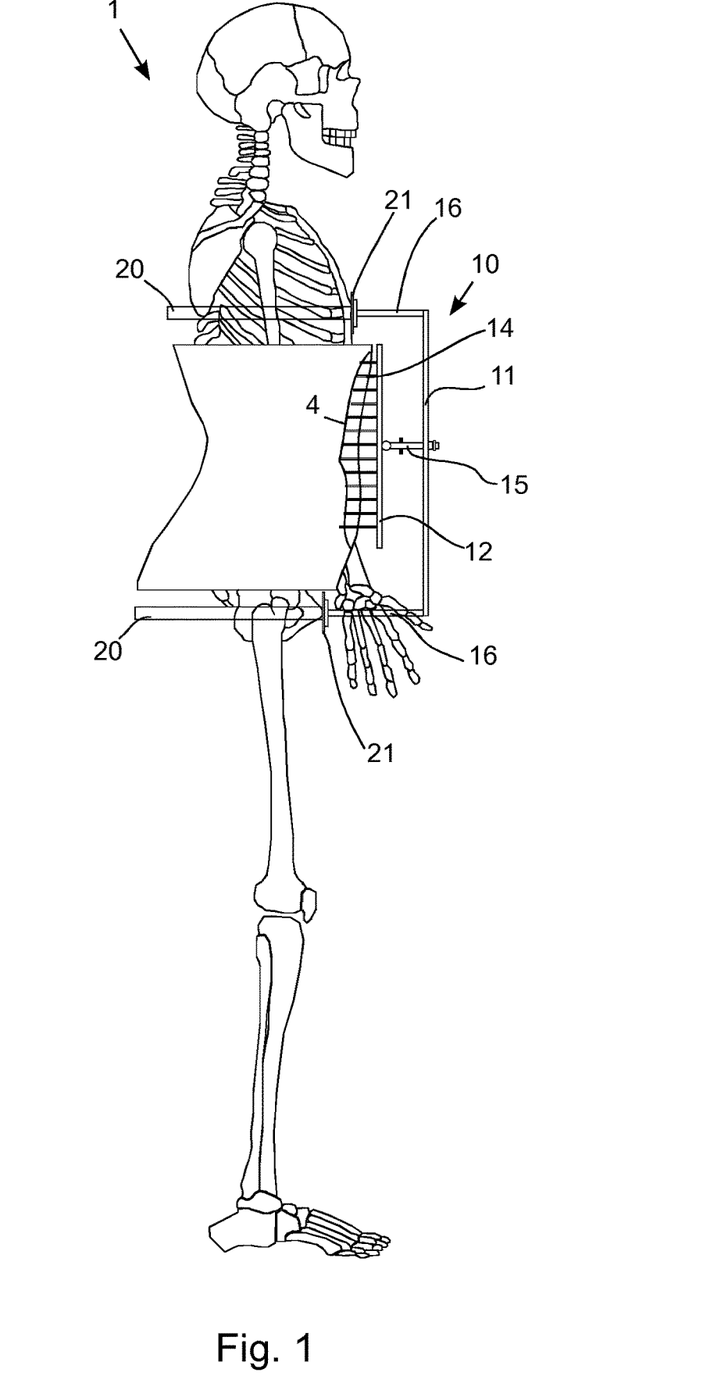
FIG. 1 is a schematic sectional drawing of a human abdomen along a sagittal plane along with a device in accordance with an embodiment of the invention when the abdomen is opened.

FIG. 1 is a schematic sectional drawing of a patient 1 along a sagittal plane. The patient 1 has a soft-tissue defect in the form of an opened abdomen. In some clinical pictures, which are associated with an intraabdominal pressure increase or an abdominal compartment syndrome, it is necessary to open the abdominal wall of the patient 1 using surgical measures. A treatment of this type with an open abdomen makes it possible to reduce the pressure within the abdomen and to remove excess gases and/or liquids from the abdomen. This may result in internal organs, for example the intestine, emerging through the abdomen opening. To counter the occurrence of infections in the abdomen and facilitate care of the open abdomen, generally the abdomen opening is provisionally sealed off, and negative pressure treatment, which will be discussed in greater detail hereinafter, is carried out simultaneously. Negative pressure treatment of this type is generally performed over a duration of a few days to a few weeks. In order for the edges of the fascia 4 not to retract excessively during this period and for it to be possible to close the fascia 4, in other words to connect the fascia edges, with unproblematic wound healing after the period with the open abdomen, a device 10 according to the invention for reducing the retraction of the fascia 4 is inserted after the abdomen is opened.

Figure 2:
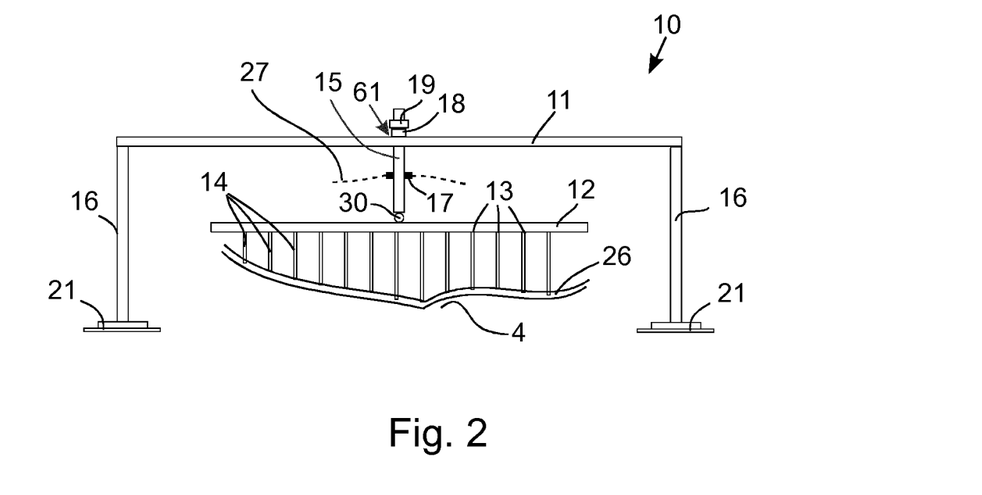
FIG. 2 is a schematic side view of the device according to FIG. 1.

As can be derived from FIGS. 1 and 2, the device 10 for reducing the retraction of the fascia 4 has a holding element 11, which can be fixed to the patient via a plurality of fastening means, in particular two, formed as props 16. The holding element 11 can thus be fixed at a first distance from the patient 1. Optionally, the props 16 may be fixed to the body of the patient via a belt fastening 20, in such a way that undesired slipping of the props 16 is prevented. The holding element 11 is formed as a bar. In the embodiment, the holding element 11 is rigidly connected to the two props 16. Alternatively, for connecting the holding element 11 to a prop 16, a joint may be arranged between the holding element 11 and the associated prop 16 in each case. The props 16 may optionally be configured variable in length, for example telescopic. On the side thereof facing the holding element 11, the props 16 each have a pressure distribution means 21 formed as a holding plate, which is positioned on the skin surface of the patient 1. By way of the pressure distribution means 21, an enlarged contact area is provided, reducing the risk of pressure points forming on the skin of the patient 1.

The device 10 further has an attachment element 12 connected to the holding element 11. The attachment element 12 is arranged at a second distance from the patient 1, which is less than the distance of the holding element 11 from the patient 1. This means that the attachment element 12 is arranged closer than the holding element 11 to the patient 1. A plurality of attachment points 13 are provided on the attachment element 12, and are formed in such a way that tension means 14, which are connected to the edge of the opened fascia 4, can be attached thereto. Via the tension means 14, tensile forces are transmitted to the edges of the fascia 4. The tension means 14 are preferably formed as threads. Alternatively, wires, cords or nets may be used. The tension means 14 may be formed resilient or non-resilient. In principle, it is possible to connect the tension means 14 directly to the fascia 4. To prevent the tension means 14 from being torn out and the fascia 4 from being damaged, the tension means 14 are preferably connected to the fascia 4 via a planar connection means formed as a net 26. The planar connection means can distribute the considerable tensile forces over a larger area and thus improve the introduction of the tensile force into the fascia 4. The planar connection means can remain connected to the fascia 4 over the entire duration of the treatment of the open abdomen. By contrast, the tension means 14 may be replaced as required.

By way of the device 10, tensile forces having a force component directed away from the body of the patient 1 are applied to the edges of the opened fascia 4 in such a way that the device 10 holds the edges tensioned and simultaneously spaced apart from one another. As a result of the tensile force, the tension of the fascia 4 is maintained during the treatment with an open abdomen, and the retraction of the edges of the fascia 4 is thus prevented. The soft-tissue defect, and thus also the fascia 4, is held open. The soft-tissue defect has an extent of more than 1 cm, preferably of more than 5 cm, in such a way that unimpeded access to the body interior is possible. After the treatment is concluded, the edges of the fascia 4 can be laid against one another and sealed directly.

The invention provides that the attachment element 12 is connected to the holding element 11 via exactly one tensile force transmission element 15, in such a way that sealing the negative pressure region during the negative pressure treatment is facilitated. The tensile force transmission element 15 is formed as a rigid tensile force transmission element 15, for example as a solid bar or hollow pipe. The tensile force transmission element 15 is connected to the attachment element 12 via a joint 30, in particular a ball joint, in such a way that the orientation of the attachment element 12 with respect to the tensile force transmission element 15 can be changed. A film 27 delimiting the negative pressure region only has to be sealed off from the tensile force transmission element 15 at one point. A sealing element 17, to which the film 27 can be fastened, is further arranged on the tensile force transmission element 15. The film 27 preferably has an opening through which the tensile force transmission element 15 can be passed. The edge of the opening is preferably formed as an adhesive edge. The film 27 can be connected to the sealing element 17 in a sealing manner via the adhesive edge. The sealing element 17 may for example be configured as a sealing ring. The sealing element 17 is rotatable with respect to the tensile force transmission element 15 and/or displaceable along the tensile force transmission element 15. It is thus possible to change the position of the tensile force transmission element 15 without damaging the film 27. It thus becomes possible to make changes to the orientation of the attachment element 12 and/or the tensile force transmission element 15 during the negative pressure treatment without major outlay.

The tensile force transmission element 15 is movable with respect to the holding element 11 in such a way that by way of the movement of the tensile force transmission element 15 the distance between the attachment element 12 and the holding element 11 can be adjusted. The tensile force transmission element 15 is mounted in a recess 61 formed as a through-opening in the holding element 11. The tensile force transmission element 15 has an external thread in an upper region positioned opposite the attachment element 11. A fastening element 19 is positioned on the external thread. The fastening element 19 has an internal thread. For example, the fastening element 19 may be formed as a nut. A compression spring is arranged between the fastening element 19 and the holding element 11, and is compressed as a function of the tensile force transmitted via the tensile force transmission element 15. The compression spring may be part of a tensile force gauge 18, in particular a spring balance, which displays the tensile force transmitted via the tensile force transmission element 15.

The fastening element 19 forms an actuation element via which the entire tensile force acting on the edges of the fascia 4 can be adjusted. The fastening element 19 is arranged in the upper region of the tensile force transmission element 15, which region is opposite the attachment element 12, in such a way that the fastening element 19 can be actuated even when negative pressure treatment is being carried out. Preferably, the fastening element 19 is formed in such a way that it can be brought from an engagement position, in which the internal thread of the fastening element 19 is engaged with the external thread of the tensile force transmission element 15, into an open position, in which the internal thread of the fastening element 19 is not engaged with the external thread of the tensile force transmission element 15. For example, the fastening element 19 may be formed as a split nut, in particular a pivotable nut.

A disconnection means, by way of which the fastening element 19 can be brought into the open position using a hand movement, is provided on the fastening element 19. In the open position, the fastening element 19 can be removed from the tensile force transmission element 15. In a further step, the holding element 11 can be removed from the patient 1, without it being necessary to detach the tension means 14 from the edge of the fascia 4. The attachment element 12, connected to the patient 1 via the tension means 14, and the tensile force transmission element 15, connected to the attachment element, remain on the patient. Detachment of this type may be necessary in particular if the region of the soft-tissue defect has to be exposed, for example so as to resuscitate the patient.

Figure 3:
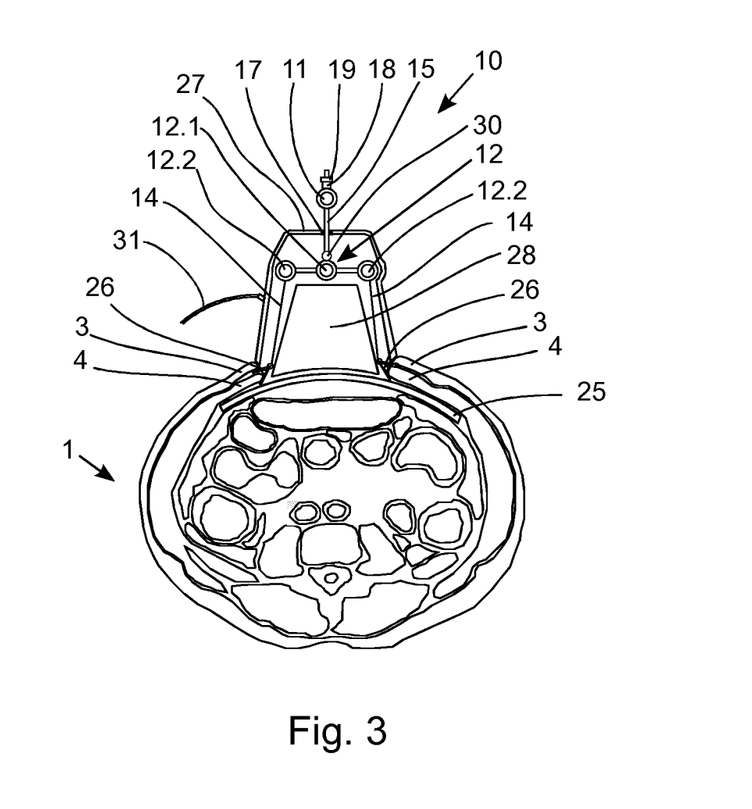
FIG. 3 is a schematic sectional drawing of a human abdomen along with a kit according to the invention for treating an open abdomen comprising a device according to FIG. 1.

As can be derived from FIG. 3, the attachment element 12 has a base part 12.1, which is connected to the tensile force transmission element 15. Two attachment regions 12.2 are connected to the base part 12.1 in such a way that they are movable with respect to the base part 12.1 and with respect to one another. The attachment regions 12.2 can be locked with respect to the base part 12.1. A plurality of attachment points 13 for tension means 14 are provided on each of the attachment regions 12.2. The tension means 14 may be attached to the attachment points 13 in that the tension means 14 are passed through a through-opening (not shown in the drawings) in the attachment region and subsequently for example knotted. An alternative attachment of the tension means 14 may take place via attachment points 13 formed as grooves. The tension means 14 may advantageously be guided through the grooves.

The base part 12.1 and the attachment regions 12.2 are formed as bars, which are arranged in particular mutually parallel. For connecting the attachment regions 12.2 to the base part 12.1, in the embodiment telescopic transverse bars are arranged between the base part 12.1 and the attachment regions 12.2.

When the negative pressure treatment is being carried out, the abdomen is for example covered by way of a sponge 25 arranged below the abdominal wall. A film (not shown in the drawings) or a separating material is preferably arranged between the sponge 25 and the intestine to prevent the intestine from drying out. A preferably further sponge 28 is introduced into the abdomen opening and the abdomen opening is sealed off using a sealing means, which is usually formed as a gas-tight film 27. The sponge 28 is connected to a vacuum pump via a suction hose 31. By way of the vacuum pump, a negative pressure is applied, in such a way that undesired liquids and/or gases can be removed from the abdomen through the suction hose 31. This negative pressure treatment is generally carried out over a duration of a few days to several weeks.

Figure 4:
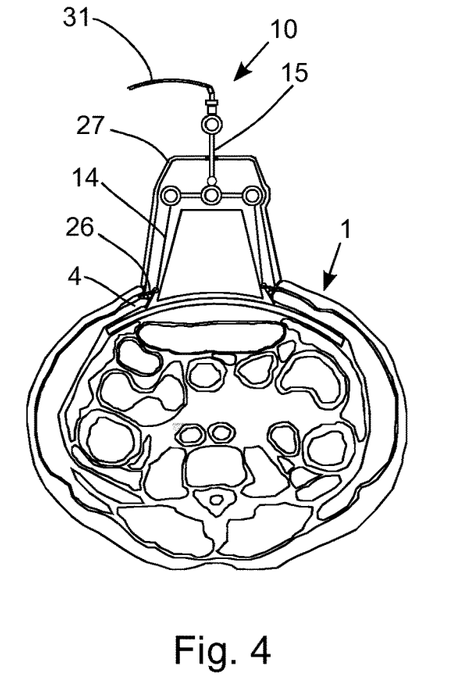
FIG. 4 is a schematic sectional drawing of a human abdomen along with a kit according to the invention for treating an open abdomen comprising a device in accordance with a second embodiment.

In an alternative embodiment shown in FIG. 4, the tensile force transmission element 15 has an air duct. The air duct may connect a first opening for attaching a vacuum pump to a second opening arranged in the region of the attachment element 12. In an embodiment of this type, it is possible to connect the suction hose 31 of the vacuum pump to the first opening of the tensile force transmission element 15 and to suck away air or liquid out of the negative pressure region through the air duct in the tensile force transmission element 15.

Figure 5:
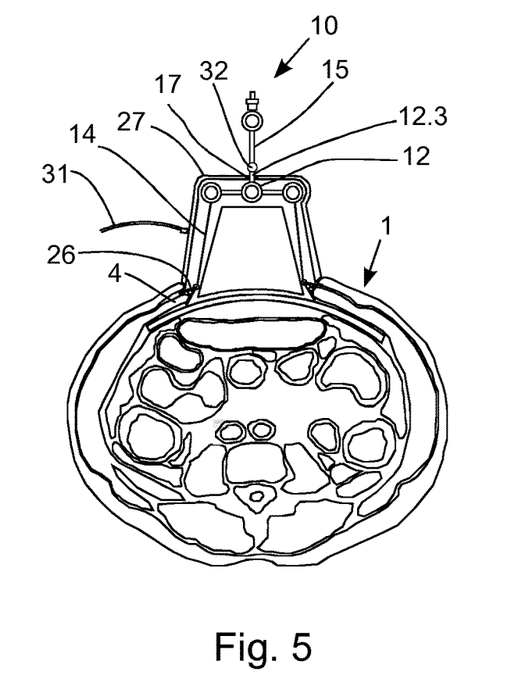
FIG. 5 is a schematic sectional drawing of a human abdomen along with a kit according to the invention for treating an open abdomen comprising a device in accordance with a third embodiment.

FIG. 5 shows a third embodiment of a device 10, the attachment element 12 being connected to the tensile force transmission element 15 via a joint 32, for example a ball joint or hinge joint. Unlike in the above-described embodiments, a sealing element 17, for example a sealing ring, is provided on the attachment element 12. The attachment element may have an in particular bar-like sealing region 12.3 on which the sealing ring 17 is arranged.

Figure 6:
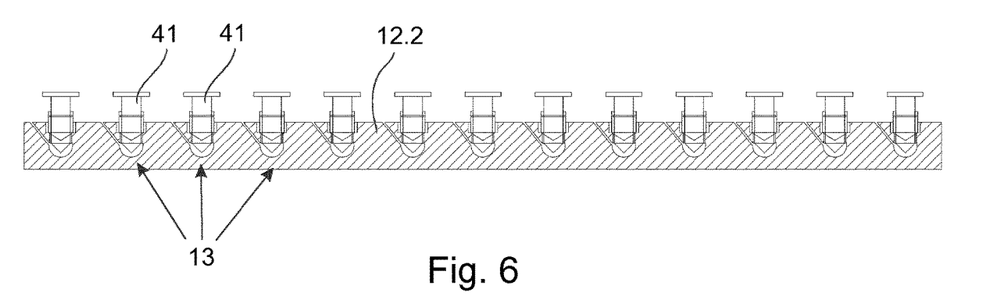
FIG. 6 is a schematic sectional drawing of an attachment region of a device according to an embodiment of the invention.

FIG. 6 shows an embodiment of an attachment region 12.2 of an attachment element 12 such as may be used in the device 10 according to the invention. The attachment region 12 has a plurality of attachment points 13, in this case thirteen, to each of which a tension means 14 can be attached. The attachment points 13 are arranged at an identical distance from one another and each have a securing element 41, via which the tension means 14 can be fixed to the attachment point 13.

Figure 7:
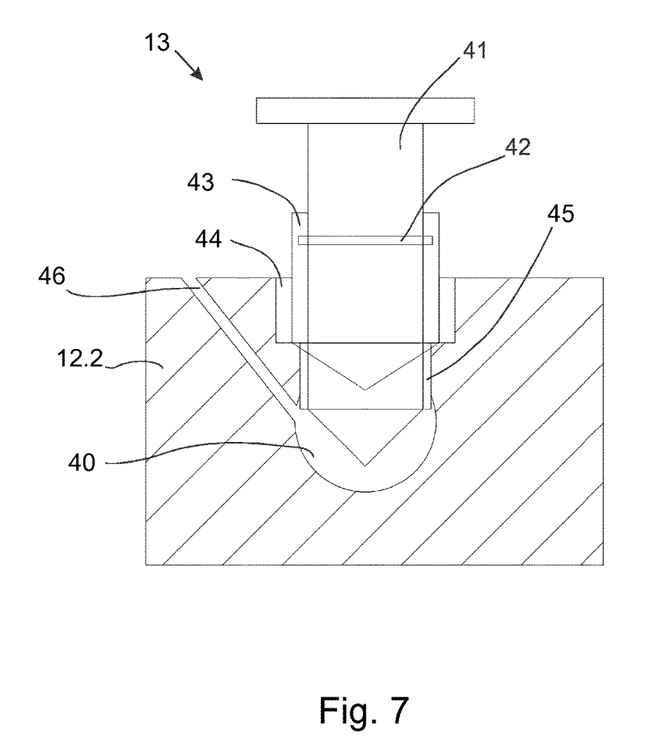
FIG. 7 is a schematic sectional drawing of an attachment point in an attachment region according to FIG. 6.

FIG. 7 is an enlarged drawing of an attachment point 13 in the attachment region 12.2 of FIG. 6. A through-hole 40 is arranged in the attachment region 12.2 of the attachment element 12. Further, an insertion groove 46 is provided, via which a tension means 14, for example a thread, can be inserted into the through-hole 40. The insertion groove 46 starts at a surface of the attachment region 12.2 and opens into the through-hole 40. A securing element 41 formed as a screw is arranged in the through-hole 40. An external thread 45 of the securing element 41 cooperates with an internal thread provided on the attachment region 12.2, in such a way that the securing element 41 can selectively be screwed into the through-opening 40 to grip the tension means 14 in place or be unscrewed from the through-hole 40 to release the tension means 14.

A guide sleeve 43 is arranged concentric with the securing element 41, and is connected to the attachment region 12.2 via a thread 44. A loss protection element 42, for example a ring, is further arranged on the securing element 41, and cooperates with an inner contour of the guide sleeve 43 in such a way that the securing element 41 cannot be removed from the attachment region 12.2. The securing element 41 can thus be prevented from undesirably falling out.

Figure 8:
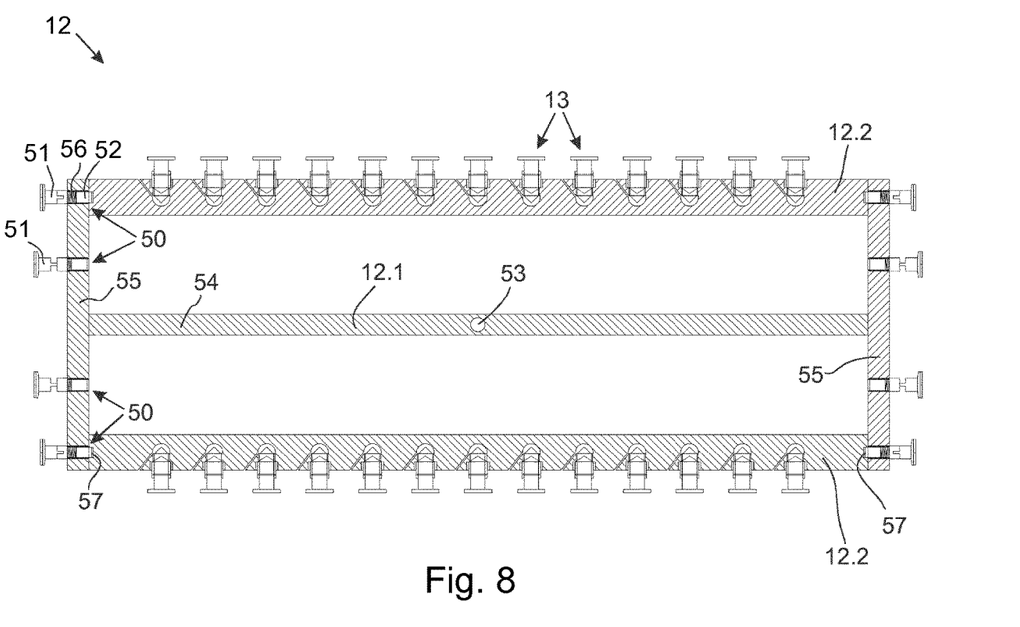
FIG. 8 is a plan view of an attachment element of a device in accordance with an embodiment of the invention in a first configuration.

FIG. 8 shows a further embodiment of an attachment 12 which can be used in the device 10 according to the invention. The attachment element 12 has a base part 12.1 and two attachment regions 12.2 which are detachable from the base part 12.1. The base part 12.1 is connected at an attachment point 53 to the single tensile force transmission element 15 (not shown here). The attachment point 53 is located in a first portion 54, which is arranged extending substantially parallel to the attachment regions 12.2. Two second portions 55 are connected to the first portion 54, and are arranged extending substantially perpendicular to the attachment regions 12.2.

The base part 12.1 has, in particular in the second portions 55 of the base part 12.1, a plurality of connection points 50, to which the attachment regions 12.2 can selectively be connected. The connection points 50 each comprise a through-hole 52, in which a securing bolt 51 is received. The securing bolts 51 can be moved between a disconnection position, in which the attachment region 12.2 can be removed from the base part 12.1, and a connection position, in which the attachment region 12.2 is fixed to the base part 12.1 via the securing bolt 51. For this purpose, a blind hole 57, in which a locking end of the securing bolt 51 engages in the connection position, is arranged on the attachment region 12.2. The securing bolt 51 is biased towards the connection position by way of a spring element 56. Further, the securing bolt 51 can be latched in the disconnection position, in particular by a rotary movement, in such a way that the connection end of the securing bolt 51 does not protrude out of the through-hole 52.

Figure 9:
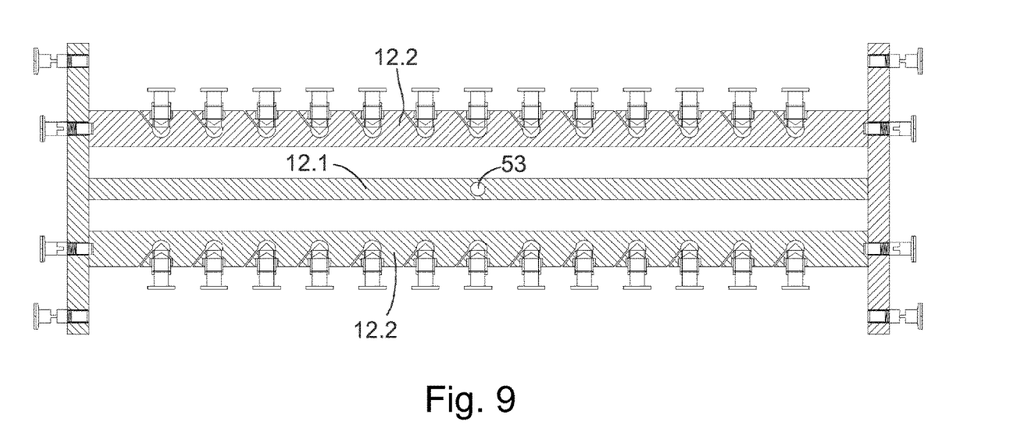
FIG. 9 is a plan view of the attachment element of FIG. 8 in a second configuration.

The connection points 50 are arranged on the two second portions 55 of the base part 12.1, in such a way that an attachment region 12.2 can be attached between every two opposite connection points 50 and connected to the connection points 50. It is thus possible to a link the connection regions 12.2 selectively to different connection points 50 on the base part 12.1 so as to change the distance between the connection regions 12.1 As a result, the device 10 can be adapted to the size of the soft-tissue defect of the patient 1. By way of example, FIG. 8 shows a first configuration of the attachment element 12, in which the attachment regions 12.2 are at a larger distance, and FIG. 9 shows a second configuration of the attachment elements 12, in which the attachment regions 12.2 are at a smaller distance.

Figure 10:
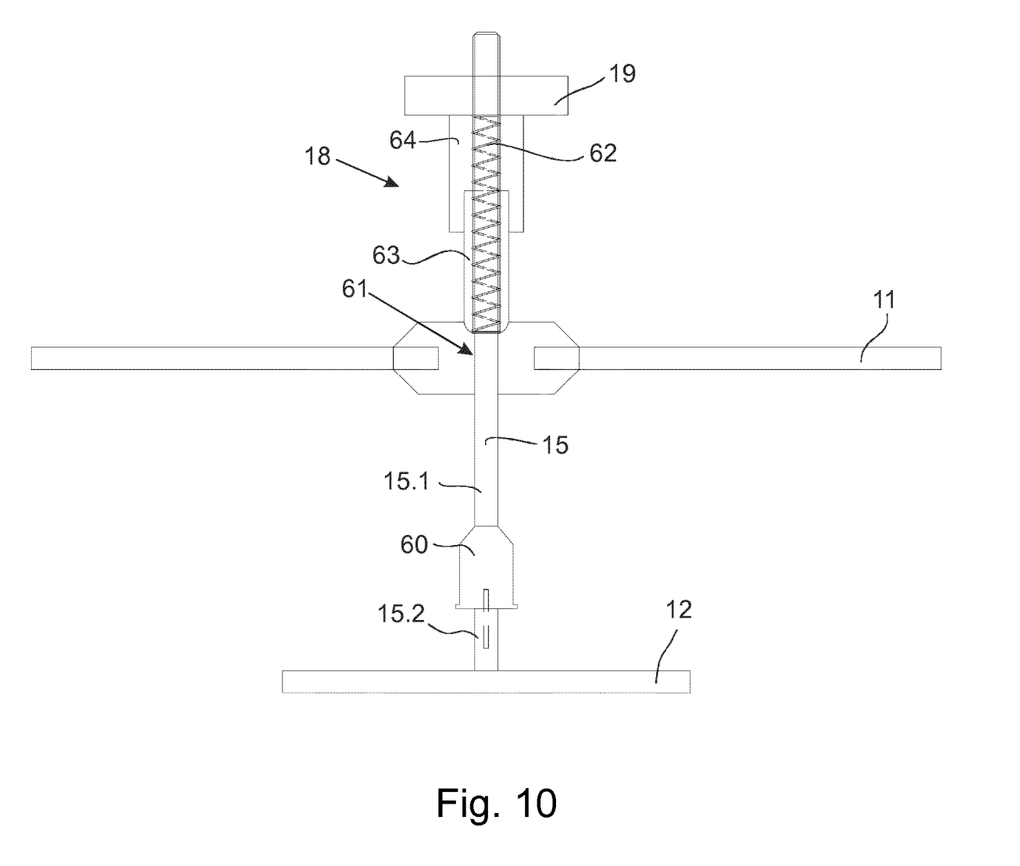
FIG. 10 is a schematic sectional drawing of a device in accordance with a fourth embodiment of the invention.

FIG. 10 shows a further embodiment of a device 10 according to the invention, in which the attachment element 12 is connected to the holding element 11 via exactly one tensile force transmission element 15. The device 10 has a plurality of props (not shown) which each connect the holding element 11 to a pressure distribution means which can be positioned on the skin of the patient. Alternatively, the props may connect the holding element 11 to an implant or a plurality of implants which are fixed to a bone of the patient.

The tensile force transmission element 15 is formed as a rigid tensile force transmission element 15 comprising two rigid parts 15.1, 15.2. The first part 15.1 and the second part 15.2 can selectively be connected to or separated from one another. For this purpose, a detachable coupling 60 is arranged between the first part 15.1 and the second part 15.2, and connects the first part 15.1 to the second part 15.2. The coupling 60 is formed as a manually detachable quick release coupling, for example as a plug-in coupling. Normally, the two parts 15.1, 15.2 of the tensile force transmission element 15 are interconnected via the coupling 60. However, if resuscitation measures have to be performed on the patient 1, the coupling 60 can be detached using only one hand movement, in such a way that access to the patient 1 is not impeded by the tensile force transmission element 15.

In the device of FIG. 10, the tensile force transmission element 15 is guided in a recess 61 in the holding element 11. In an upper region opposite the attachment element 11, the tensile force transmission element 15 has an external thread. A fastening element 19 is positioned on the external thread. The fastening element 19 has an internal thread. For example, the fastening element 19 may be formed as a thread.

The device further has a tensile force gauge 18, by way of which the tensile force transmitted via the tensile force transmission element 15 can be measured. The tensile force gauge 18 is arranged between the holding element 11 and the fastening element 19 positioned on the tensile force transmission element 15. The tensile force gauge 18 has a compression spring 62, which comprises a first spring end, mounted stationary with respect to the holding element 11, and a second spring end, mounted stationary with respect to the fastening element 19 positioned on the external thread of the tensile force transmission element 15. The first spring end is positioned on the holding element 11, and the second spring end is positioned on the fastening element 19.

The tensile force gauge 18 comprises a scale sleeve 63 and an indicator sleeve 64, which are arranged movable with respect to one another concentric with the tensile force transmission element 15. The scale sleeve 63 has a plurality of regions, in particular three, which are provided with different colours and/or hatchings and/or symbols. The diameter of the indicator sleeve 64 is greater than the diameter of the scale sleeve 63, in such a way that the indicator sleeve 64 can enclose the scale sleeve 63 from the outside. The indicator sleeve 64 is positioned on the fastening element 19 and the scale sleeve 63 is positioned on the holding element 11.

Figure 11:
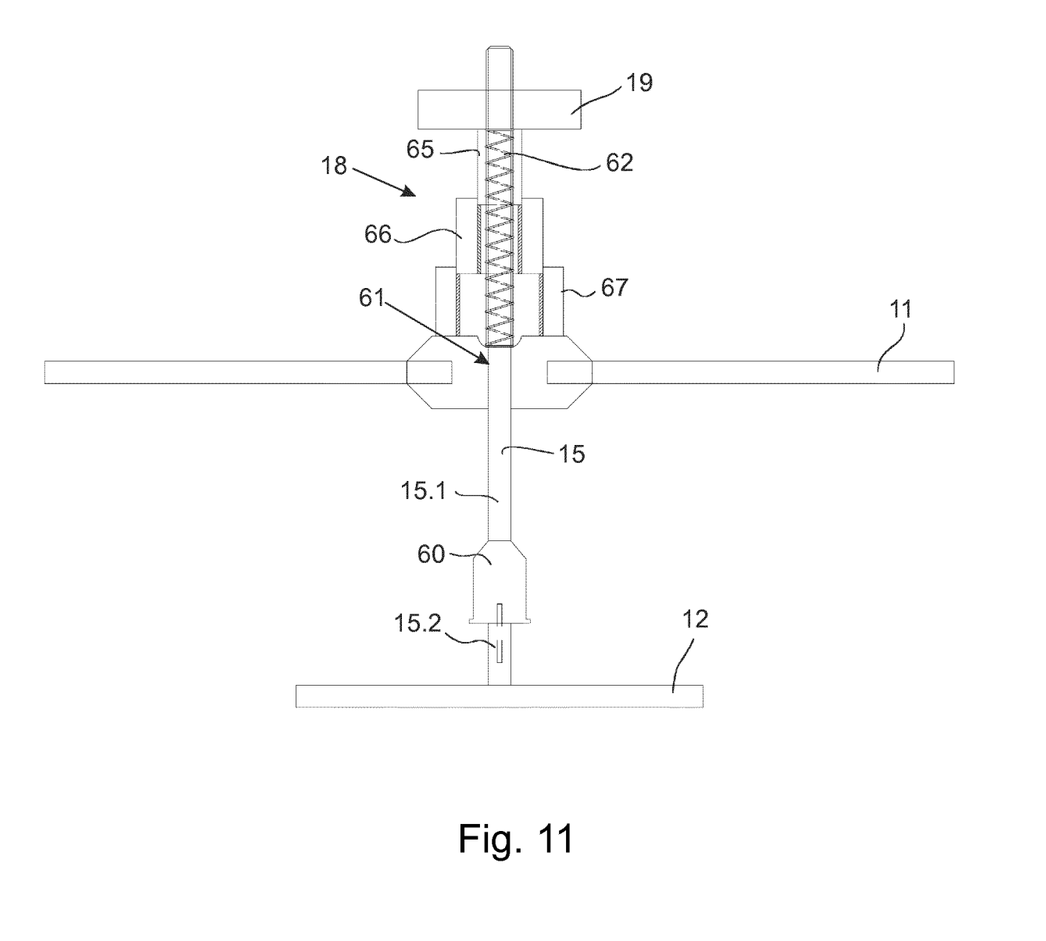
FIG. 11 is a schematic sectional drawing of a device in accordance with a fifth embodiment of the invention.

FIG. 11 shows a further embodiment of a device 10 according to the invention. Just as in the embodiment of FIG. 10, the tensile force transmission element 15 is formed in two parts, the two parts 15.1, 15.2 of the tensile force transmission element 15 being interconnected via a manually detachable coupling 60. Unlike the device 10 shown in FIG. 10, the tensile force gauge 18 has three sleeves 65, 66, 67, which are arranged movable with respect to one another concentric with the tensile force transmission element 15. The sleeves 65, 66, 67 are provided with different colours and/or hatchings and/or symbols, in such a way that a relative display of the tensile force being transmitted via the tensile force transmission element 15 is possible.

By way of the device 10 according to the invention, in accordance with the embodiments, shown in the drawings, the fascia 4 can be held sufficiently far open that the body interior, in particular the abdomen or the space positioned within the soft-tissue defect, is accessible and/or the internal organs can emerge at least substantially unimpeded through the open soft-tissue defect, in particular the abdominal wall opening or an open soft tissue defect on the back. Further, the device 10 may be used to stretch a fascia 4 of which the edges have already retracted. The device according to the invention may optionally be used without negative pressure wound treatment being performed.

LIST OF REFERENCE NUMERALS

1 Patient
3 Skin
4 Fascia
10 Device for reducing the retraction of the fascia
11 Holding element
12 Attachment element
12.1 Base part
12.2 Attachment region
12.3 Sealing region
13 Attachment points
14 Tension means 15 Tensile force transmission element
16 Prop
17 Sealing element
18 Tensile force gauge
19 Fastening element
20 Belt fastening
21 Pressure distribution means
25 Sponge
26 Net
27 Film
28 Sponge
30 Joint
31 Suction hose for vacuum pump
40 Through-hole
41 Securing element
42 Loss protection element
43 Guide sleeve
44 Thread
45 External thread
46 Insertion groove
50 Connection point
51 Securing bolt
52 Through-hole
53 Attachment point
54 Portion
55 Portion
56 Spring element
57 Blind hole
60 Coupling
61 Recess
62 Compression spring
63 Scale sleeve
64 Indicator sleeve
65, 66, 67 Sleeve

The invention claimed is:

1. Device for reducing retraction of edges of an opened fascia of a patient having an open soft-tissue defect, the device having:
    a holding element configured to be fixed at a first distance from the patient,
    an attachment element connected to the holding element and configured to be fixed at a second distance from the patient while the holding element is fixed at the first distance from the patient, the second distance is less than the first distance, the attachment element has a plurality of attachment points configured for attaching tensioning means, which is configured to be connected to an edge of the opened fascia, and
    exactly one tensile force transmission element located in between the holding element and the attachment element, the exactly one tensile force transmission element connects the holding element to the attachment element, the exactly one tensile force transmission element being configured to transmit a tensile force from the attachment element and the plurality of attachment points to the holding element.

2. Device according to claim 1, wherein the exactly one tensile force transmission element is guided in a recess in the holding element.

3. Device according to claim 1, wherein a sealing element that is a sealing ring is arranged on the exactly one tensile force transmission element.

4. Device according to claim 1, wherein the exactly one tensile force transmission element has an air duct.

5. Device according to claim 4, wherein the air duct connects a first opening for attaching a vacuum pump to a second opening arranged in a region of the attachment element.

6. Device according to claim 1, wherein the device has a tensile force gauge that is a spring balance for measuring the tensile force transmitted via the exactly one tensile force transmission element.

7. Device according to claim 6, wherein the tensile force gauge has a compression spring, which comprises a first spring end, which is mounted stationary with respect to the holding element, and a second spring end, which is mounted stationary with respect to a catch of the exactly one tensile force transmission element or with respect to a fastening element positioned on an external thread of the exactly one tensile force transmission element.

8. Device according to claim 6, wherein the tensile force gauge has a scale sleeve and an indicator sleeve, which are arranged movable with respect to one another concentric with the exactly one tensile force transmission element.

9. Device according to claim 6, wherein the tensile force gauge has three or more sleeves, which are arranged movable with respect to one another concentric with the exactly one tensile force transmission element.

10. Device according to claim 1, wherein the exactly one tensile force transmission element is formed rigid.

11. Device according to claim 1, wherein the attachment element is detachably connected to the holding element.

12. Device according to claim 1, wherein the exactly one tensile force transmission element has a first part and a second part, which can selectively be connected to or disconnected from one another.

13. Device according to claim 12, wherein a detachable coupling is arranged between the first part and the second part and connects the first part to the second part.

14. Device according to claim 13, wherein the detachable coupling is detachable manually.

15. Device according to claim 1, wherein the attachment element has two attachment regions, the two attachment regions each having the plurality of attachment points, and a distance between the two attachment regions is adjustable.

16. Device according to claim 15, wherein the attachment element has a base part, and the two attachment regions are movable with respect to the base part.

17. Device according to claim 16, wherein the two attachment regions are detachable from the base part.

18. Device according to claim 15, wherein the attachment element has a base part, the two attachment regions being detachable from the base part and a plurality of connection points, to which the two attachment regions can selectively be connected, being provided on the base part.

19. Device according to claim 18, wherein, at the connection points, the base part has through-holes in each of which a securing bolt is arranged.

20. Device according to claim 1, wherein the attachment element has two attachment regions, the two attachment regions each having the plurality of attachment points, and the two attachment regions are movable with respect to one another.

21. Device according to claim 1, wherein the device has a plurality of props which each connect the holding element to a pressure distribution means, which can be positioned on skin of the patient.

22. Device according to claim 1, wherein the device has a plurality of props, which connect the holding element to an implant or a plurality of implants which can be fixed to a bone of the patient.

23. Device according to claim 1, wherein the attachment element has a through-hole and an insertion groove opening into the through-hole, via which a tension means is configured to be inserted into the through-hole, in a region of each of the attachment points.

24. Kit for treating an open soft-tissue defect, comprising:
the device according to claim 1, and
at least one sponge for filling out the soft-tissue defect.

25. Kit according to claim 24, wherein the kit comprises a sealing means for sealing off the soft-tissue defect which has an opening for passing the exactly one tensile force transmission element through, the sealing means having an adhesion means in a region of the opening.

26. Device according to claim 1, wherein a tension means is configured to be inserted into a through-hole of the attachment element.

27. Device according to claim 26, wherein the tension means are connected to the opened fascia via a net.

* * * * *